(12) United States Patent
Ortlepp

(10) Patent No.: US 10,362,945 B2
(45) Date of Patent: Jul. 30, 2019

(54) METHOD AND DEVICE FOR ASCERTAINING A BLOOD PRESSURE CURVE

(71) Applicant: CIS FORSCHUNGSINSTITUT FUER MIKROSENSORIK GMBH, Erfurt (DE)

(72) Inventor: Hans-Georg Ortlepp, Apfelstaedt (DE)

(73) Assignee: CIS FORSCHUNGSINSTITUT FUER MIKROSENSORIK GMBH, Erfurt (DE)

( * ) Notice: Subject to any disclaimer, the term of this patent is extended or adjusted under 35 U.S.C. 154(b) by 0 days.

(21) Appl. No.: 15/578,201

(22) PCT Filed: May 12, 2016

(86) PCT No.: PCT/EP2016/060735
§ 371 (c)(1),
(2) Date: Nov. 29, 2017

(87) PCT Pub. No.: WO2016/192952
PCT Pub. Date: Dec. 8, 2016

(65) Prior Publication Data
US 2018/0146865 A1 May 31, 2018

(30) Foreign Application Priority Data
May 29, 2015 (DE) .................... 10 2015 108 518

(51) Int. Cl.
*A61B 5/021* (2006.01)
*A61B 5/024* (2006.01)
*A61B 5/00* (2006.01)

(52) U.S. Cl.
CPC ...... *A61B 5/02108* (2013.01); *A61B 5/02416* (2013.01); *A61B 5/7239* (2013.01)

(58) Field of Classification Search
CPC ............ A61B 5/02108; A61B 5/02416; A61B 5/7239; A61B 5/021; A61B 5/02116;
(Continued)

(56) References Cited

U.S. PATENT DOCUMENTS

| | | | |
|---|---|---|---|
| 6,616,613 B1 * | 9/2003 | Goodman | A61B 5/0002 600/504 |
| 8,211,030 B2 * | 7/2012 | Donehoo | A61B 5/022 600/485 |

(Continued)

FOREIGN PATENT DOCUMENTS

DE    10 2008 002 747 A1    12/2009

OTHER PUBLICATIONS

Sachiko Homma et al: "Relati onship Between Accelerated Plethysmogram, Blood Pressure and Arteriolar Elasticity", Tai Ryoku Kagaku, vol. 41, No. I, Jan. 1, 1992 (Jan. 1, 1992), pp. 98-107 with English language abstract (10 pages total).
(Continued)

*Primary Examiner* — Navin Natnithithadha
(74) *Attorney, Agent, or Firm* — Karin L. Williams; Mayer & Williams PC

(57) ABSTRACT

The invention relates to a method and a device for ascertaining a time-dependent blood pressure curve. Time- and volume-dependent blood flow values are detected in a noninvasive manner in a tissue section with a good blood flow as photoplethysmography values P(t) using a photoplethysmography sensor. A data processing unit transforms the photoplethysmography values P(t) into blood pressure values B(t) by carrying out a transformation rule. An output and storage unit at least temporarily stores the transformed blood pressure values B(t) as time-dependent blood pressure values and transfers said values to an external or internal display and/or storage unit arranged downstream.

11 Claims, 2 Drawing Sheets

(58) Field of Classification Search
CPC .............. A61B 5/02125; A61B 5/0215; A61B 5/02154; A61B 5/024; A61B 5/02405; A61B 5/02422; A61B 5/0255; A61B 5/02; A61B 5/7253; A61B 5/7257; A61B 5/726
USPC ........ 600/481, 483, 485, 486, 488, 500–504
See application file for complete search history.

(56) References Cited

U.S. PATENT DOCUMENTS

| | | | | |
|---|---|---|---|---|
| 8,463,347 | B2* | 6/2013 | Watson | A61B 5/021 600/324 |
| 8,602,997 | B2* | 12/2013 | Banet | A61B 5/02125 600/485 |
| 8,740,802 | B2* | 6/2014 | Banet | A61B 5/02125 600/485 |
| 8,808,188 | B2* | 8/2014 | Banet | A61B 5/02125 600/485 |
| 8,825,428 | B2* | 9/2014 | Addison | A61B 5/02125 702/98 |
| 9,060,695 | B2* | 6/2015 | Peters | A61B 5/0205 |
| 9,161,700 | B2* | 10/2015 | Banet | A61B 5/02125 |
| 9,215,986 | B2* | 12/2015 | Banet | A61B 5/02125 |
| 9,668,656 | B2* | 6/2017 | Banet | A61B 5/02125 |
| 9,687,159 | B2* | 6/2017 | Ochs | A61B 5/0205 |
| 2009/0326386 | A1* | 12/2009 | Sethi | A61B 5/021 600/480 |
| 2010/0160798 | A1* | 6/2010 | Banet | A61B 5/02125 600/490 |
| 2010/0324387 | A1* | 12/2010 | Moon | A61B 5/746 600/324 |
| 2010/0324388 | A1* | 12/2010 | Moon | A61B 5/746 600/324 |
| 2012/0029320 | A1* | 2/2012 | Watson | A61B 5/02125 600/301 |
| 2012/0029363 | A1* | 2/2012 | Lund | A61B 5/02108 600/485 |
| 2012/0179011 | A1* | 7/2012 | Moon | A61B 5/7207 600/324 |
| 2013/0253341 | A1* | 9/2013 | Sethi | A61B 5/021 600/485 |
| 2013/0296674 | A1* | 11/2013 | Watson | A61B 5/021 600/324 |
| 2014/0012147 | A1* | 1/2014 | Li | A61B 5/021 600/494 |
| 2014/0142445 | A1* | 5/2014 | Banet | A61B 5/02007 600/493 |
| 2014/0276145 | A1* | 9/2014 | Banet | A61B 5/02125 600/490 |
| 2015/0057554 | A1* | 2/2015 | Watson | A61B 5/02125 600/485 |

OTHER PUBLICATIONS

International Search Report and Written Opinion dated Aug. 30, 2016, issued in connection with corresponding International Application No. PCT/EP2016/060735 (11 pages total).

* cited by examiner

- Prior art -

METHOD AND DEVICE FOR ASCERTAINING A BLOOD PRESSURE CURVE

FIELD

The present invention relates to a method and device for ascertaining a time-dependent blood pressure curve in the human or animal bloodstream.

BACKGROUND

Measurement data relating to arterial stiffness and central blood pressure play an ever greater in assessing cardiovascular risks. Established medical diagnostic systems (SphygmoCor, Complior, Arteriograph) use piezoelectric, tonometric, or oscillometric measuring methods for obtaining such data from the blood pressure wave occurring in the circulation. Measuring methods of this kind can depict the time behavior of the blood pressure in a peripheral artery with such detail that the blood pressure function (pressure over time) can be reliably separated into individual subcomponents, even if they partially overlap. Usually, the first subcomponent is interpreted as a direct wave and the second is interpreted as a wave that is reflected at the branch into the two large pelvic arteries. The magnitudes of the two components and their time difference are then diagnostically relevant. Based on the time difference and the (doubled) length of the aorta, it is possible to calculate the pulse wave velocity, which depends on the blood pressure and vascular condition.

Various publications have explored the correlations between blood pressure and certain features of the photoplethysmographically depicted pulses. These studies focused on either the time difference between the so-called R wave of an additionally detected EKG and the starting point of the pulse wave or shape features of the pulse wave alone, determined without an EKG.

A photoplethysmogram (PPG) is generally understood to be an optically obtained plethysmogram, i.e. the measurement of a volumetric measurement of an organ. With regard to the present invention, a photoplethysmogram is depicted in order to determine the volumetric change in blood vessels, which is dependent on the blood pressure wave occurring in the circulation. Photoplethysmographic values can, for example, be detected using pulse oximeters, which supply a volume-dependent measurement value based on changes in light absorption in peripheral tissue through which blood circulates.

DE 10 2008 002 747 A1, for example, has disclosed a pulse oximeter in the form of an ear sensor. The ear sensor is used to monitor at least one physiological measurand by means of a noninvasive measurement in the ear canal. To do so, the ear sensor has a plurality of optoelectronic components, which are arranged in a housing that can be inserted into the ear canal, with the plurality of optoelectronic components being distributed around the periphery of the housing.

US 2013/0253341 A1 describes a device and method for noninvasive continuous blood pressure determination. To accomplish this, the data processing in a conventional photoplethysmographic measuring system is enhanced in order to enable continuous noninvasive blood pressure determination. It is apparent, however, that the photoplethysmographic pulse wave is significantly smoother than the peripheral blood pressure wave that was obtained according to the above-mentioned methods. For this reason, much fewer details can be distinguished in the photoplethysmographically determined pulse wave.

Particularly with the previously known photoplethysmographically functioning methods, it separation into direct and reflected subcomponents is not possible. Blood pressure changes can only be determined based on changes in relatively extensively blurred shape features. But since these features are also dependent on other variable physiological influencing factors, it is necessary to carry out a regular calibration with a reference blood pressure measuring system.

US 2014/0012147 describes a device and method for continuous noninvasive blood pressure measurement, which should enable an automatic recalibration. In this case, reference is made to a duration $\Delta T$ between a first and second maximum in the signal curve, but this could not be brought into relation to the above-mentioned pulse wave transit time.

U.S. Pat. No. 6,616,613 B1 discloses a device and method for monitoring physiological signals such as the blood volume contour. To achieve this, a photoplethysmographic sensor is positioned on a user's body part. Based on the electrical signals of the sensor, physiological parameters are determined that are then processed. Non-pulsatile and slowly pulsing signals are filtered out from the blood volume contour. Characteristics of the user's aortal reflected wave contour are extracted from a volume contour, with the volume contour being selected from the blood volume contour and the filtered blood volume contour. The characteristics of the user's aortal reflected wave contour are determined in part from the fourth derivative of the volume contour. The physiological parameters are shown to the user.

SUMMARY

Basically, it must be stated that known methods for displaying a blood pressure wave can only be used under clinical conditions and/or only for a short time. The differences in the signal curve that arise with the use of conventional measuring methods are illustrated in FIG. 1. The solid line therein shows the typical pressure curve of a peripheral blood pressure wave of the kind that is recorded with a suprasystolic pressure sensor. The dashed line, by contrast, shows the photoplethysmogram (PPG) simultaneously recorded in the same organism using a noninvasively functioning ear sensor. The depiction shows that the first two maxima in the peripheral pressure wave (solid curve) are quite pronounced and can be attributed to the above-described direct and reflected components. The time difference between the maxima can be reliably determined and interpreted as a doubled pulse wave transit time. The third maximum in the peripheral pressure wave comes from the dicrotic wave. By contrast, in the photoplethysmogram (dashed curve), only the dicrotic wave stands out as a distinguishable component. With methods know from the prior art, it is not possible based on the photoplethysmogram to reliably determine a time interval from which the pulse wave transit time could be determined.

The object of the present invention, therefore, is to disclose a method and device with which it is possible, based on a photoplethysmogram or based on photoplethysmographically obtained measurement values, to simply and reliably ascertain the time-dependent curve of the blood pressure, i.e. the peripheral blood pressure wave.

This object is attained by means of a method according to the attached claim 1 and devices according to claims 6 and 10.

In order to ascertain the time-dependent curve of the blood pressure, according to the invention, time-dependent and volume-dependent blood flow values at a suitable section of tissue through which blood flows in the form of photoplethysmographic values P(t) are detected in a noninvasive way in a first step, namely by means of a photoplethysmographically functioning sensor. A photoplethysmogram is thus virtually recorded as a prefiltered time series. This can be carried out with known means or sensors provided that they have a sufficiently good signal-to-noise ratio.

Preferably, this detection of photoplethysmographic values P(t) is carried out in the ear, for example on the earlobe or in the outer ear canal, preferably on the tragus, by means of an ear sensor. Other sensors and measurement points, however, can also be suitable.

In a second step, a transformation of the photoplethysmographic values P(t) in blood pressure values B(t). Surprisingly, it has turned out that the respective sum of a photoplethysmographic value P(t), its first time derivative, and its second time derivative must first be calculated, with all three summands being respectively acted on with predetermined coefficients. The determination of the coefficients is described in greater detail below. From a mathematical standpoint, the transformation to be performed can be described by means of the following transformation formula:

$$B(t) = k0 \cdot P(t) + k1 \cdot P'(t) + k2 \cdot P''(t), \text{ with}$$

the first derivative $P'(t) = \dfrac{dP}{dt}$ the second derivative $P''(t) = \dfrac{d^2 P}{dt^2}$ predetermined coefficients $k0, k1, k2$;

In this second step of the method according to the invention, a linear transformation of the photoplethysmographic pulse into an image of the peripheral blood pressure wave is thus carried out.

And lastly, in a final step, the transformed blood pressure values B(t) are output as time-dependent blood pressure values, for example to a display and/or memory unit. This can be followed by an additional evaluation and derivation of diagnostic information according to known methods and rules for processing data from blood pressure wave measurements.

A device according to the invention for ascertaining the time-dependent curve of the blood pressure, particularly in the human bloodstream, is configured so that it permits execution of the above-described method. In order to achieve this, a device according to the invention includes a photoplethysmographic sensor, which noninvasively detects time-dependent and volume-dependent blood flow values in a peripheral blood vessel in the form of photoplethysmographic values P(t). In addition, a data processing unit is provided, which transforms the photoplethysmographic values P(t) into blood pressure values B(t), for which purpose in particular the transformation instruction already mentioned above is implemented. This implementation can be carried out through the use of signal processors and/or a software implementation. Finally, the device includes an output and memory unit, which at least temporarily stores the transformed blood pressure values B(t) in the form of time-dependent blood pressure values and relays them to a subordinate external or internal display and/or memory unit.

The coefficients k0, k1, k2 are dependent on the specific physiological influence factors. They can easily be determined by means of a reference measurement in which the peripheral blood pressure wave is recorded in a conventional way and is compared to the one ascertained according to the invention. Once the coefficients are established, they can be used unchanged for all further measurements under the same or comparable conditions. With high precision requirements, the coefficients can be established as personal values for each individual patient. With suitable field measurements, however, it is also possible to establish generally applicable coefficients for certain patient groups.

For better comprehension of the invention, the details and modification options of the transformation step will be explained in particular below. According to a preferred embodiment, the linear transformation can be carried out by folding with a suitable correlator, which is composed of difference quotients.

To achieve this, the noninvasively obtained measurement values are used to produce digitized photoplethysmographic values $P_i$ with N measurement points and i=1 . . . N, in the time grid $\Delta t$. The above-mentioned general formula for the transformation of the photoplethysmographic values into the blood pressure values can be represented as follows with the use of the time series representation for the blood pressure wave $B_i$, valid for i=2 . . . N−1:

$$B_i = k0 \cdot P_i + k1 \cdot P_i' + k2 \cdot P_i''$$

Based on the existing discrete measurement values, the derivatives required for the transformation are generated in a particularly simple way as difference quotients:

$$P_i' = \frac{P_{i+1} - P_{i-1}}{2 \cdot \Delta t} \text{ and } P_i'' = \frac{P_{i-1} - 2P_i + P_{i+1}}{(\Delta t)^2}$$

If the difference quotients are inserted into the transformation formula, this yields:

$$B_i = k0 \cdot P_i \frac{k1}{2 \cdot \Delta t}(P_{i+1} - P_{i-1}) + \frac{K2}{(\Delta t)^2}(P_{i-1} - 2 \cdot P_i + P_{i+1})$$

This formula can be resorted according to $P_{i-1}$, $P_i$, and $P_{i+1}$, in order to obtain a FIR-transformation filter (filter with finite pulse response), which is describe by the following:

$$B_i = G_{-1} \cdot P_{i-1} + G_0 \cdot P_i + G_1 \cdot P_{i+1}, \text{ with}$$

constant weighting factors:

$$G_{-1} = \frac{-k1}{2 \cdot \Delta t} + \frac{k2}{(\Delta t)^2},$$

$$G_0 = k0 - \frac{2 \cdot k2}{(\Delta t)^2},$$

$$G_1 = \frac{k1}{2 \cdot \Delta t} + \frac{k2}{(\Delta t)^2}.$$

A significant advantage to this calculation method lies primarily in the fact that for each value determination $B_i$, it is not necessary to perform the mathematically complex determination of the first and second derivatives. Instead, it is sufficient to carry out these complex calculations one time when determining the weighting factors $G_{-1}$, $G_0$, and $G_1$. The weighting factors can then be used for all of the other transformation steps.

In this case, an FIR filter is preferably implemented in the data processing unit in order to implement the device according to the invention.

According to a preferred embodiment, a signal prefiltering takes place for the purpose of transforming the measured raw values $PR_i$ into prefiltered values $P_i$. In a particularly preferred embodiment, this can be carried out with the aid of a FIR low pass filter with 2k+1 coefficients $TP_j$, =-k . . . k.

In order to be able to achieve an error-free execution of the combining of the coefficients shown below, 2 zero values must be provided at the limits of the filter function: $TP_{-k}=TP_k=0$. The prefiltering is carried out according to the formula:

$$P_i = \sum_{j=-k}^{k} TP_j \cdot PR_{i-j}$$

According to a once-again modified, advantageous embodiment, the prefiltering and the transformation are carried out combined into one calculation step, which can be mathematically described as follows: The prefiltering formula for $P_{i-1}$, $P_i$, and $P_{i+1}$ is inserted into the above-mentioned formula of the transformation filter $$B_i = G_{-1} \cdot P_{i-1} + G_0 \cdot P_i + G_1 \cdot P_{i+1}:$$

$$B_i = G_{-1} \cdot \sum_{j=-k}^{k} TP_j \cdot PR_{i-j-1} + G_0 \cdot \sum_{j=-k}^{k} TP_j \cdot PR_{i-j} + G_1 \cdot \sum_{j=-k}^{k} TP_j \cdot PR_{i-j+1}.$$

Combined into a sum:

$$B_i = \sum_{j=-k}^{k} TP_j \cdot (G_{-1} \cdot PR_{i-j-1} + G_0 \cdot PR_{i-j} + G_1 \cdot PR_{i-j+1}).$$

Combining of the coefficients:

$$KF_j = G_{-1} \cdot TP_{j-1} + G_0 \cdot TP_j + G_1 \cdot TP_{j+1}.$$

Thus yielding the following for the transformation filter:

$$B_i = \sum_{j=-k+1}^{k-1} KF_j \cdot PR_{i-j},$$

where the prefiltering and transformation are carried out in a combined FIR filter pass with the 2k−1 coefficients $KF_j$, where j=−k+1 . . . k−1.

A particularly preferred embodiment improves the suppression of long-wave fluctuations in the pressure wave signal. In photoplethysmographic measurement curves, the signal base level usually fluctuates over a longer time, which can result in evaluation problems. In order to correct for long-wave trends, a sliding average value over a suitable time interval is usually generated, which is subtracted from the measurement curve or the measurement values are divided by it. To generate a trend-corrected image of the blood pressure curve, this correction can be carried out either before or after the transformation demonstrated above.

A modified embodiment of the method also features the fact that in addition to the determination of the time-dependent curve of the blood pressure, i.e. the generation of the image of the blood pressure wave from the photoplethysmogram, the pulse wave transit time is also derived from the generated image of the blood pressure wave.

The usual methods for breaking down a pressure wave, which has been measured according to the prior art, into partial waves can also be used on the blood pressure wave image generated according to the invention. Consequently, the previously known methods are used on the value curve that has been ascertained according to the invention. It is advantageous if the adaptation of the curve is situated in the range prior to the insertion of the incisure with two sub-curves of a suitable model function, which describes a preferably asymmetrical bell curve. The time difference of its starting points or maxima is interpreted as the pulse wave transit time.

If the photoplethysmogram has been recorded with a sensor that can be worn for a long time such as an in-ear sensor, then this enables a long-term monitoring of the pulse wave transit time. A preferred embodiment of the device thus features the fact that it is configured for long-term monitoring, in particular with the provision of sufficient storage capacity for storing the data detected.

Based on the physiology of the cardiovascular system, it is known that elevated blood pressure increases cardiovascular risk and that as blood pressure increases, the pulse wave velocity rises. Usually, the pulse wave velocity is ascertained from the pulse wave transit time by means of a conversion formula into which the body size is fed. Consequently, monitoring the pulse wave transit time with the method according to the invention also enables a risk warning with the occurrence of high blood pressure. A corresponding preferably embodied device features the fact that it includes a signal output unit, which outputs a warning signal if the time interval between the occurrences of the first of the two peaks in the transformed blood pressure values B(t) falls below a predetermined minimum time interval. Since the second peak is located on the foothill of the first (in this regard, see FIG. 3), the determination requires a breakdown into components. Only after the transformation of the PPG signal according to the invention are the two peaks visible and can a breakdown into components occur.

BRIEF DESCRIPTION OF THE DRAWINGS

Other details that contribute to comprehension of the invention ensue from the accompanying figures.

DETAILED DESCRIPTION

Figure 1:
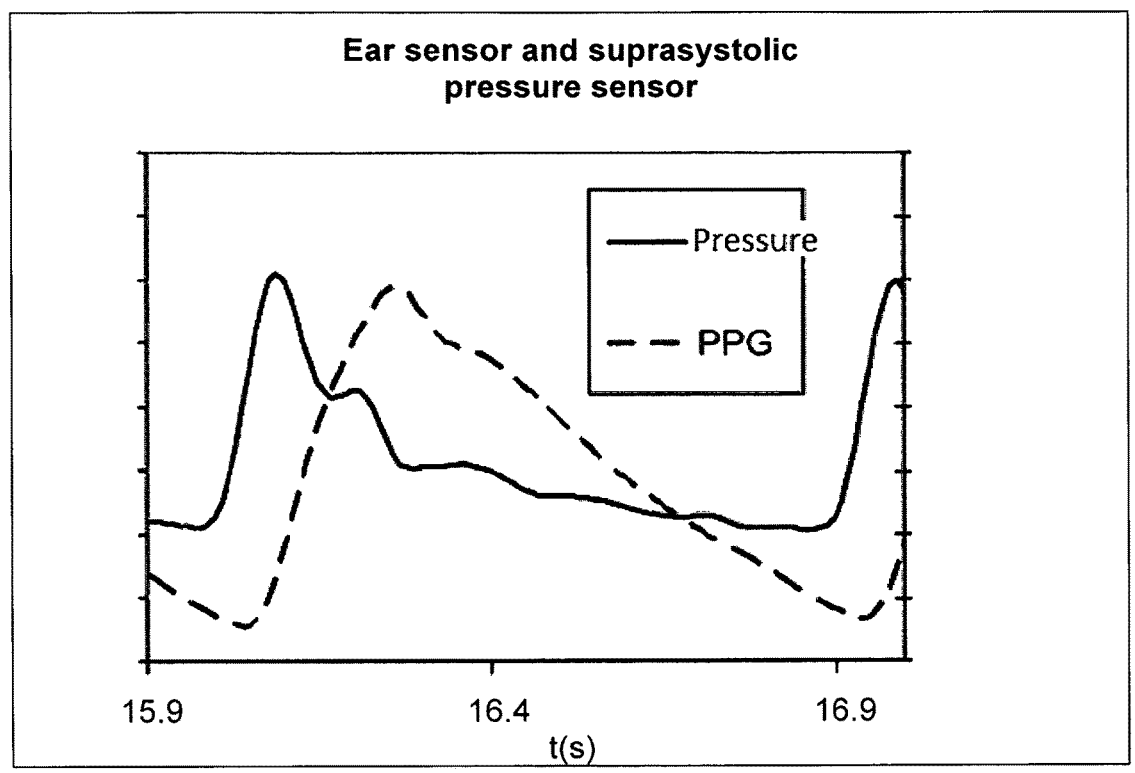
FIG. 1 shows a pressure curve measured with a supra-systolic pressure sensor compared to a photoplethysmogram recorded with an ear sensor (prior art)

The curves shown in FIG. 1 and their meaning have already been explained above with reference to the prior art.

Figure 2:
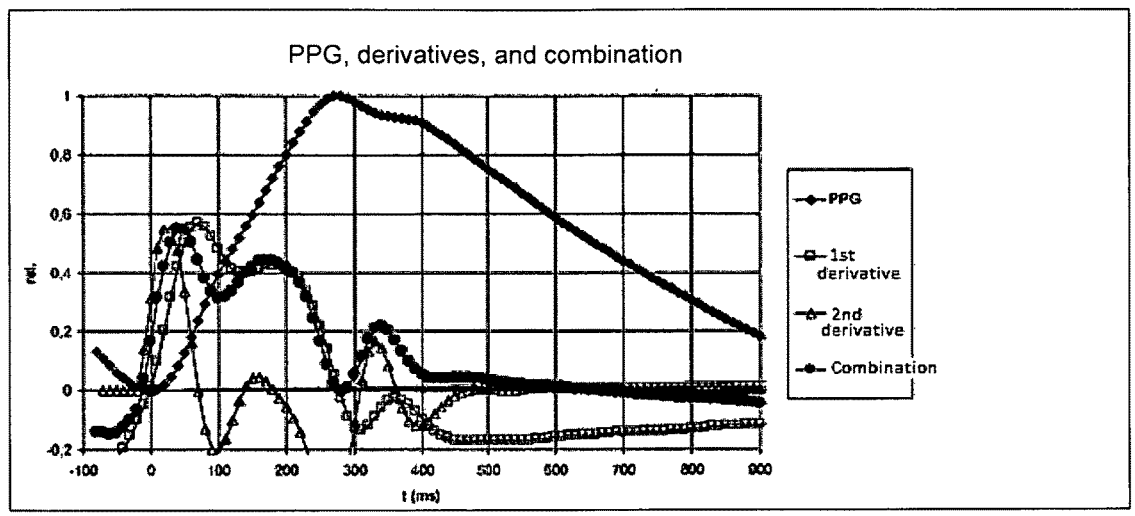
FIG. 2 shows a transformation of a photoplethysmogram (PPG) into an image of a blood pressure wave.

In FIG. 2, it is possible to reconstruct the curve of a transformation to be carried out according to the invention of a photoplethysmogram (PPG) into an image of a blood pressure wave based on the depicted curves. The measurement data were recorded using an ear sensor with a data rate of 100 samples/second. The figure shows the curve of the photoplethysmogram (PPG) recorded with the sensor, the calculated first derivative and second derivative, and the resulting curve of the blood pressure as a combination according to the formulas explained above.

Figure 3:
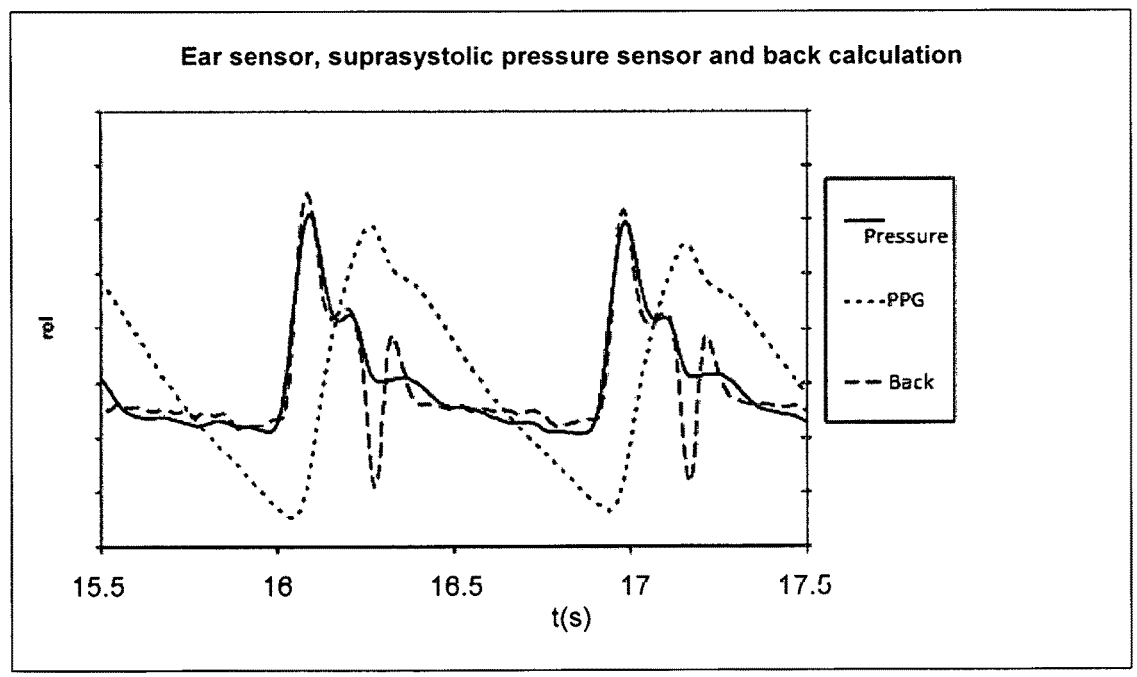
FIG. 3 shows the comparison of a direct pressure measurement with the image of the blood pressure wave produced from the photoplethysmogram with the aid of the method according to the invention.

FIG. 3 shows a comparison of a direct pressure measurement by means of suprasystolic pressure wave measurement (solid line) to the image of the blood pressure wave generated from the photoplethysmogram with the aid of the method according to the invention (dashed line). The high correlation between the direct pressure measurement and the progression of the pressure curve ascertained using the method according to the invention is readily apparent.

The invention claimed is:

1. A method for ascertaining the time-dependent curve of the blood pressure including the following steps:
noninvasive detection of time-dependent and volume-dependent blood flow values, in the form of photoplethysmographic values P(t), in a section of tissue with blood circulation by means of a photoplethysmographically functioning sensor;
transformation of the photoplethysmographic values P(t) into blood pressure values B(t) through the use of the following transformation formula by means of a data processing unit:

$$B(t) = k0 \cdot P(t) + k1 \cdot P'(t) + k2 \cdot P''(t), \text{ with}$$

the first derivative $P'(t) = \dfrac{dP}{dt}$ the second derivative $P''(t) = \dfrac{d^2 P}{dt^2}$ predetermined coefficients $k0, k1, k2$;

determining the time interval between the occurrences of the first two peaks in the curve of the transformed blood pressure values B(t) within a signal period by means of the data processing unit;
outputting of the transformed blood pressure values B(t) as time-dependent blood pressure values to a display and/or memory unit; and
generating a warning signal if the time interval falls below a predetermined minimum time interval in order to signal a critical blood pressure by means of a signal output unit.

2. The method according to claim 1, wherein
digitized photoplethysmographic values $P_i$ with N measurement points and $i=1 \ldots N$ are generated,
the first and second derivatives are generated as difference quotients:

$$P'_i = \dfrac{P_{i+1} - P_{i-1}}{2 \cdot \Delta t} \text{ and } P''_i = \dfrac{P_{i-1} - 2P_i + P_{i+1}}{(\Delta t)^2}$$

the transformation, converted through the insertion of difference quotients, is used in the form:

$$B_i = G_{-1} \cdot P_{i-1} + G_0 \cdot P_i + G_1 \cdot P_{i+1}$$

with constant weighting factors:

$$G_{-1} = \dfrac{-k1}{2 \cdot \Delta t} + \dfrac{k2}{(\Delta t)^2},$$

$$G_0 = k0 - \dfrac{2 \cdot k2}{(\Delta t)^2},$$

$$G_1 = \dfrac{k1}{2 \cdot \Delta t} + \dfrac{k2}{(\Delta t)^2}.$$

3. The method according to claim 2 wherein the photoplethysmographic values P(t) are detected in the outer ear canal, preferably on the inside of the tragus.

4. The method according to claim 2 wherein the coefficients are established by means of a calibration measurement, either for an individual patient or for a group of patients.

5. The method according to claim 1, wherein the photoplethysmographic values P(t) are detected in the outer ear canal, preferably on the inside of the tragus.

6. The method according to claim 5 wherein the coefficients are established by means of a calibration measurement, either for an individual patient or for a group of patients.

7. The method according to claim 1, wherein the coefficients are established by means of a calibration measurement, either for an individual patient or for a group of patients.

8. A device for ascertaining the time-dependent curve of the blood pressure, including:
a photoplethysmographic sensor, which noninvasively detects time-dependent and volume-dependent blood flow values, in the form of photoplethysmographic values P(t), in a section of tissue with blood circulation;
a data processing unit, which transforms the photoplethysmographic values P(t) into blood pressure values B(t), by executing the following transformation instruction:

$$B(t) = k0 \cdot P(t) + k1 \cdot P'(t) + k2 \cdot P''(t), \text{ with}$$

the first derivative $P'(t) = \dfrac{dP}{dt}$ the second derivative $P''(t) = \dfrac{d^2 P}{dt^2}$ predetermined coefficients $k0, k1, k2$;

an output and memory unit, which at least temporarily stores the transformed blood pressure values B(t) in the form of time-dependent blood pressure values and relays them to a subordinate external or internal display and/or memory unit; and
a signal output unit configured to issue a warning signal if the time interval between the occurrences of the first two peaks in the curve of the transformed blood pressure values B(t) falls below a predetermined minimum time interval.

9. The device according to claim 8, wherein the photolethysmographic sensor is selected from the following group:
an ear sensor, which detects the photoplethysmographic values P(t) in the outer ear canal, preferably on the tragus; and
a fingertip sensor, which detects the photoplethysmographic values P(t) at a fingertip.

10. The device according to claim 9, wherein an FIR filter is implemented in the data processing unit.

11. The device according to claim 8, wherein an FIR filter is implemented in the data processing unit.

* * * * *